United States Patent [19]

Smith

[11] 4,088,648
[45] May 9, 1978

[54] BIS 1,4-(B-VINYLSO$_2$-PROPIONYL)-PIPERAZINE

[75] Inventor: Norman Alfred Smith, Hornchurch, England

[73] Assignee: Ciba-Geigy AG, Basel, Switzerland

[21] Appl. No.: 734,782

[22] Filed: Oct. 22, 1976

[30] Foreign Application Priority Data

Oct. 31, 1975  United Kingdom ............... 45279/75

[51] Int. Cl.$^2$ ............................................. C07D 295/18
[52] U.S. Cl. ..................................... 544/387; 96/111; 260/112 R; 260/117
[58] Field of Search ..................................... 260/268 C

[56] References Cited

U.S. PATENT DOCUMENTS

| | | | |
|---|---|---|---|
| 2,288,197 | 6/1942 | Kranzlein et al. | 260/268 C |
| 2,541,584 | 2/1951 | Jacoby | 260/268 C |
| 3,798,222 | 3/1974 | Senning et al. | 260/268 C |

*Primary Examiner*—Jose Tovar
*Attorney, Agent, or Firm*—Burgess, Dinklage & Sprung

[57] ABSTRACT

A vinylsulphone compound of the formula

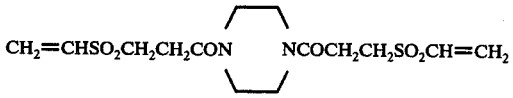

is provided. This compound is useful as cross-linking agent for hydrophilic colloids, especially for gelatin which is in the form of layers of photographic materials.

1 Claim, No Drawings

BIS 1,4-(B-VINYLSO₂-PROPIONYL)-PIPERAZINE

This invention relates to a novel vinylsulphone compound, to its production and to its use as a cross-linking agent for hydrophilic colloids.

According to the present invention there is provided a vinylsulphone compound of the formula

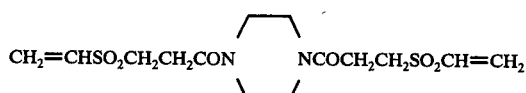
(1)

The compound of formula (1) is prepared by reacting 2 molar proportions of 3-(2-chloroethylsulphonyl)-propionyl chloride with 1 molar proportion of piperazine in a basic organic solution to produce the compound of the formula

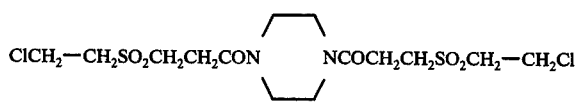
(2)

and then dehydrochlorinating this compound to produce the compound of formula (1).

Chloroethylsulphonyl compounds may be dehydrochlorinated to the corresponding vinylsulphonyl compounds in a number of different ways which are well known. An example of such a conversion is given in U.S. Pat. No. 3,868,257 wherein triethylamine is used.

3-(2-Chloroethylsulphonyl)-propionic acid may be prepared by the method described in French patent specification No. 1,363,046 wherein 2-chloroethylsulphinic acid is reacted with acrylic acid and 3-(2-chloroethylsulphonyl)-propionyl chloride may be prepared therefrom by reaction with thionyl chloride.

The vinylsulphone compound of formula (1) is of particular use in cross-linking hydrophilic colloids.

Therefore according to another aspect of the present invention there is provided a process for cross-linking hydrophilic colloids which contain amino, imino and/or hydroxyl groups characterised in that the compound of the formula (1) is incorporated into the colloid to effect cross-linking thereof.

The cross-linking process of the present invention can be used in the textile and leather industry, the manufacture of paper and the plastics, glue and gelatin industry. Above all, it can be used as a process for hardening water-soluble colloids for example polyvinyl alcohol, gelatin or gelatin derivatives, especially when these colloids are in the form of layers in photographic materials. The reaction of these colloids with the vinylsulphone compound of use in the present invention in general takes place easily, and in the usual manner. The vinylsulphone compound is water-soluble and thus can be used as an aqueous solution. In most cases in order to carry out the cross-linking process of the present invention it suffices to add the vinylsulphone compound of the present invention as an aqueous solution or in a solid form which is as finely divided as possible, to an aqueous solution of the hydrophilic colloid, with good stirring.

Thus, a solution of the vinylsulphone cross-linking agent in water, or mixed with, for example, ethanol, methanol or acetone, can be brought together with the colloids at normal or slightly raised temperature. Gelatin, which optionally may contain silver halide and/or other components required to produce photographic images, has proved particularly suitable for cross-linking by the process of the present invention.

The coating solution which is an aqueous solution containing both gelatin and the vinylsulphone cross-linking agent can, in the usual way, be coated on a substrate to form a layer, and be dried. The layer can then be left at elevated temperature or at room temperature for a certain time, for example up to 24 hours. Thereupon cross-linking, which is evidenced by hardening of the layer, takes place rapidly and progressively this is shown by the melting point of the gelatin being raised substantially, for example from 25° to 60° C, and by the reciprocal swelling factor increase.

The amount of the vinylsulphone cross-linking agent used depends on the desired degree of hardening of the gelatin layer required but is suitably from 0.1 to 10 percent by weight based on the weight of the dry gelatin.

A particular advantage of the process of the present invention is that when the vinylsulphone cross-linking agent is used at a low concentration it imparts a sufficient degree of hardness to the gelatin layers in 18 to 24 hours, so that the coated material can be tested by processing a sample immediately following its manufacture, even if the test be carried out at a raised temperature or in strong processing baths.

It is a further advantage that during the process of the present invention, no significant change in pH of the gelatin layer occurs.

The cross-linking or hardening effect itself is very stable; even after prolonged storage at room temperatures around 40° C and at a relative atmospheric humidity of about 70%, the reciprocal swelling factor remains above 0.2 (compare the Table in Example II).

Further the degree of hardening is also not changed significantly by acids or bases even on prolonged action, which indicates that the hardener-gelatin bond created has great resistance to hydrolysis.

The vinylsulphone compound of the present invention is furthermore generally sufficiently soluble in water and sufficiently stable in aqueous solutions to enable the process of the present invention to be used in the preparation of photographic material. Thus, for example it is particularly desirable — for the continuous manufacture of photographic materials — that batches of solutions of cross-linking agents should remain stable at room temperature for several hours or days and that the concentration should not decrease or should only do so insignificantly. Also it is important that in the coating solution, at about 40° C, the hardener should undergo very little or no decomposition and very little or no reaction with water during the requisite standing time and dwell time, so as to maintain its full cross-linking action over the course of several hours, during coating, drying and storage of the photographic material.

Furthermore, the viscosity of the coating solution should not significantly increase during the standing time as a result of the addition of the hardener. It is also particularly important that even on prolonged treatment of the coated layer at raised temperature and atmospheric humidity conditions the hardener should not cause any yellowing, fogging of photographic material or effect the contrast graduation of the material on development.

The vinylsulphone compound of the present invention fulfils the above desiderata very well.

In particular it hydrolyses very little when present in an aqueous solution. It does not discolour gelatin. When this compound is added to a gelatin solution it causes only a small increase in the viscosity of the solution and thus such solution can be coated without difficulty. The compound has a good hardening effect over a wide pH range and thus can be used in the preparation of a wide range of photographic materials. This is shown in Example I which follows.

Thus the process of the present invention is suitable for hardening (cross-linking) all the layers in photographic material containing gelatin for example, intermediate layers, emulsion layers, base layers, top layers, backing layers and anti-halation layers. The layers can contain not only the cross-linking agents but also additives of the most diverse kind for example, silver halide, pigments, such as barium sulphate, titanium dioxide or silicon dioxide or those of organic nature, such as coloured pigments, and also image dyestuffs, colour coupling agents, latices, sensitisers, filter dyestuffs, anti-halation dyestuffs and light screening dyestuffs, emulsion stabilisers, UV absorbers, optical brighteners and even other cross-linking agents.

The present invention not only includes the novel vinylsulphone of formula (1), the process for preparing this compound, the process for cross-linking hydrophilic colloids using the vinylsulphone of formula (1) but also includes hydrophilic colloids cross-linked by the above cross-linking process and in particular includes layers containing gelatin so cross-linked especially gelatino silver halide emulsion layers and other layers in photographic material as well as the photographic material containing such layers.

The following Example I shows the preparation of the vinylsulphone compound of formula (1) and Example II shows the use of this compound in cross-linking gelatin, a hydrophilic colloid.

EXAMPLE I 8.76 g 3-(2-chloroethylsulphonyl)-propionyl chloride was dissolved in 100 ml dry dichloroethane. A solution of 1.72 g anhydrous piperazine and 4.04 g triethylamine in 60 ml of dichloroethane was added dropwise at 10° to 15° C over ½ hour. The mixture was stirred for a further 1½ hours at 10° to 15° C then cooled in ice and filtered. The solid was washed with dichloroethane, dried and then recrystallised from ethanol/water. Yield 6.2 g. Melting point: 188° to 189° C.

6.12 g of the above product was suspended in a mixture of 100 ml ethanol and 30 ml water at 50° C. 2.83 g triethylamine was added and the mixture stirred for 1 hour at 50° C. The solution was filtered and the filtrate evaporated under reduced pressure. The residue was recrystallised from ethanol. Yield 3.4 g. Melting point: 175° to 180° C.

EXAMPLE II

In the Example which follows, the reciprocal swelling factor is used as a measure of the hardening. The samples were prepared as follows:

6 ml of a 3% strength gelatine solution, 1 ml of a 1% strength dyestuff solution of the formula

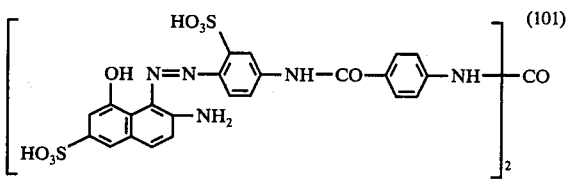

1 ml of $25 \times 10^{-3}$ molar solution of the vinylsulphone as prepared in Example I and 5 ml of deionised water are mixed and the pH adjusted to 4.5 to 7.5. The solution is coated on a $13 \times 18$ cm triacetate film. After solidification at 10° C, the layer is dried over the course of 2 hours at approx 20° C. (The dyestuff merely serves to make the samples more readily visible during the swelling measurements).

Some samples of the coated film were stored under room conditions (NK, approx. 20° C, 50% relative atmospheric humidity) and other samples were incubated (CL, 43° C, 69% relative atmospheric humidity).

To determine the reciprocal swelling factor, a thin section of approx 20 μ is prepared from each of the samples and measured under a microscope. The thickness of the dry gelatin layer is then determined, deionised water is then added and after 4 minutes the thickness of the swollen gelatin layer is measured. The reciprocal swelling factor 1/SF corresponds to the following ratio:

$$1/SF = \frac{\text{Thickness of the dry layer}}{\text{Thickness of the swollen layer}}$$

The results of the coatings are shown in the table below:

Table

| Coating pH | Storage | 1/SF |  |  |  |
|---|---|---|---|---|---|
|  |  | 1 day | 2 days | 7 days | 14 days |
| 4.5 | NK | 0.060 | 0.077 | 0.109 | 0.200 |
|  | CL | — | 0.199 | 0.244 | 0.289 |
| 5.5 | NK | 0.114 | 0.164 | 0.236 | 0.323 |
|  | CL | — | 0.263 | 0.323 | 0.309 |
| 6.5 | NK | 0.188 | 0.218 | 0.272 | 0.350 |
|  | CL | — | 0.300 | 0.350 | 0.370 |
| 7.5 | NK | 0.222 | 0.242 | 0.285 | 0.360 |
|  | CL | — | 0.325 | 0.349 | 0.369 |

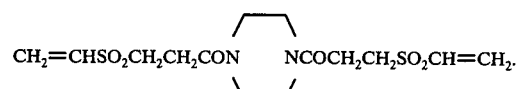

I claim:
1. A vinylsulphone compound of the formula